United States Patent [19]

Biedermann et al.

[11] Patent Number: 5,725,527

[45] Date of Patent: Mar. 10, 1998

[54] ANCHORING MEMBER

[75] Inventors: Lutz Biedermann, Villingen; Jürgen Harms, Karlsruhe, both of Germany; Harry L. Shufflebarger, Miami, Fla.

[73] Assignee: Biedermann Motech GmbH, Schwenningen, Germany

[21] Appl. No.: 625,405

[22] Filed: Mar. 27, 1996

Related U.S. Application Data

[63] Continuation of Ser. No. 244,397, filed as PCT/EP93/02756, Oct. 8, 1993, Pat. No. 5,545,165.

[30] Foreign Application Priority Data

Sep. 10, 1992 [DE] Germany ............................ 42 34 118.3

[51] Int. Cl.⁶ ............................................. A61B 17/70
[52] U.S. Cl. ..................... 606/61; 606/65; 606/72; 606/73; 606/60
[58] Field of Search ......................... 606/60, 61, 72, 606/73, 65

[56] References Cited

U.S. PATENT DOCUMENTS

| | | | |
|---|---|---|---|
| 4,641,636 | 2/1987 | Cotrel | 128/69 |
| 4,653,481 | 3/1987 | Howland et al. | 128/69 |
| 4,815,453 | 3/1989 | Cotrel | 128/69 |
| 5,005,562 | 4/1991 | Cotrel | 128/69 |
| 5,042,982 | 8/1991 | Harms et al. | 606/61 |
| 5,067,955 | 11/1991 | Cotrel | 606/73 |
| 5,129,388 | 7/1992 | Vignaud et al. | 606/61 |
| 5,176,680 | 1/1993 | Vignaud et al. | 606/61 |
| 5,217,497 | 6/1993 | Mehdian | 623/17 |
| 5,261,913 | 11/1993 | Marnay | 606/61 |
| 5,312,404 | 5/1994 | Asher et al. | 606/61 |
| 5,352,224 | 10/1994 | Westermann | 606/61 |
| 5,360,429 | 11/1994 | Jeanson et al. | 606/61 |
| 5,443,467 | 8/1995 | Biedermann et al. | 606/72 |
| 5,545,165 | 8/1996 | Biedermann et al. | 606/73 |

FOREIGN PATENT DOCUMENTS

| | | |
|---|---|---|
| 0346521A1 | 7/1988 | European Pat. Off. |
| 0 346 521 A1 | 12/1989 | European Pat. Off. |
| 0 441 729 A1 | 2/1991 | European Pat. Off. |
| 0441791A1 | 2/1991 | European Pat. Off. |
| 0487830A1 | 8/1991 | European Pat. Off. |
| WO 91/16020 | 10/1991 | European Pat. Off. |
| 0 465 158 AS | 1/1992 | European Pat. Off. |
| 0 465 158A2 | 1/1992 | European Pat. Off. |
| 0 487 830 A1 | 6/1992 | European Pat. Off. |

(List continued on next page.)

OTHER PUBLICATIONS

Surgical Technique and Taking Spinal Instrumentation To A New Dimension (1988).

Improvements in C–D Instrumentation, 1988 Proceeding of the International Congress on Cotrel–Dubousset Instrumentation, pp. 233–239.

Decision of the Federal Circuit, Dated Jan. 24, 1996 (95–1209) Sofamor Danek Group, Inc. v. Deputy–Motech, Inc.

*Primary Examiner*—Michael Buiz
*Assistant Examiner*—Daphna Shai
*Attorney, Agent, or Firm*—George W. Neuner

[57] ABSTRACT

An anchoring member is provided which comprises a shaft 2 to be fastened to a bone and a head 3 for connection with a rod 10, the head having a substantially U-shaped cross-section and being connected with the shaft 2 at the base 5 thereof, the head further comprising two free legs 6, 7 defining a channel 4 for receiving the rod 10. The free legs 6, 7 are provided with an internal thread 8 extending in direction of the legs. A fastening member 11 and a member 12 embracing the legs at the outside thereof are provided. In order to allow not only straight rods, but also curved rods to be received and thus to allow an individual adaptation to the conditions of the spinal column to be treated the free legs have an external thread 9 and the member 12 has an internal thread cooperating therewith. The fastening member 11 comprises a thread cooperating with the internal thread 8 to allow the fastening member to be screwed in.

7 Claims, 2 Drawing Sheets

FOREIGN PATENT DOCUMENTS

| | | |
|---|---|---|
| 2 624 720 | 12/1987 | France . |
| 2 624 720 | 6/1989 | France . |
| 2 650 173 | 2/1991 | France . |
| 2 659 546 A1 | 9/1991 | France . |
| 39 16 198 C2 | 11/1990 | Germany . |
| 41 07 480 A1 | 9/1992 | Germany . |
| 2-500091 | 1/1990 | Japan . |
| 2-500091 | 2/1990 | Japan . |
| WO 89/00028 | 1/1989 | WIPO . |
| WO 91/16020 | 10/1991 | WIPO . |

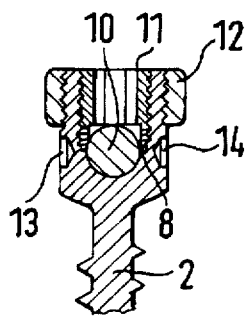
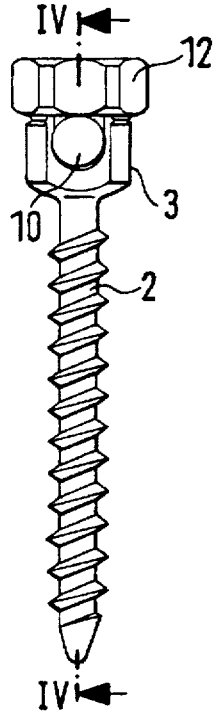
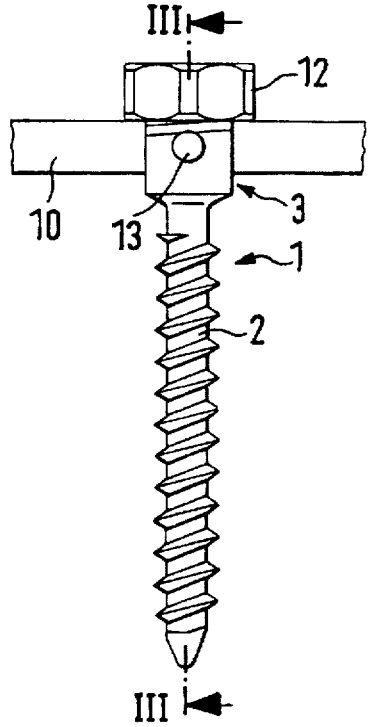
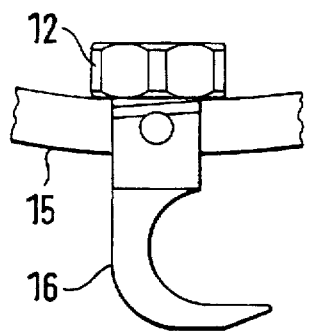
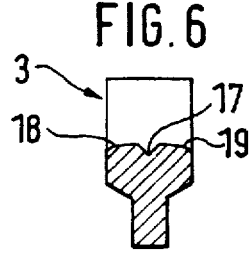
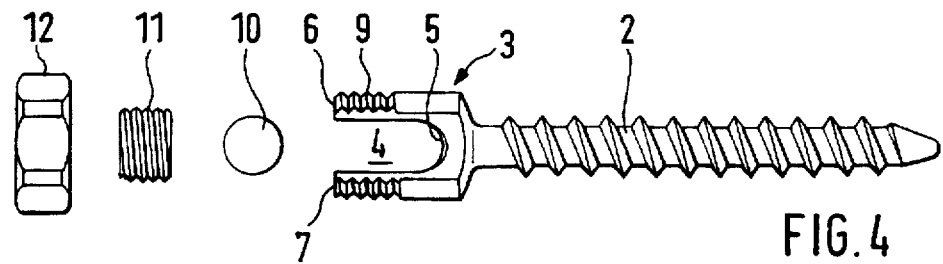

ANCHORING MEMBER

This is a continuation of application Ser. No. 08/244,397 filed on May 20, 1994, now U.S. Pat. No. 5,545,165, which is a 371 application of International Application PCT/EP93/02756, filed on Oct. 8, 1993 designating the United States.

The invention relates to an anchoring member with a shaft to be fastened to a bone and a head for connection with a rod, the head having a substantially U-shaped cross-section which has its base connected to the shaft and comprises two free legs defining a channel for receiving the rod, wherein the legs comprise an internal thread and an external thread, and with a member embracing the legs at their outer side and having an internal thread cooperating with the external thread, and with a fastening member having a thread cooperating with the internal thread of the legs.

Such an anchoring member is known from document EP-A-0,487,830. The rod comprises a triangular cross-section and serves as a restraint from torsional motions. The longitudinal stabilisation proper is provided by plates which are curved corresponding to the intended shape correction. By nature the plates are comparatively space-consuming. Further, the base between both legs is formed flat in longitudinal direction of the slit. In a practical application there is a considerable repeated alternating stress caused by the forces acted onto the rod. Hence, the rods tend to break after some time at the edges of the slit base.

It is the object of the invention to form the anchoring member in such a manner that the size of the anchor can be reduced and the anchor resists to higher continuous stresses. This is of particular importance, because such anchoring members and the rods to be connected thereto are used as components for correction implants for the human spinal column and small dimensions and an unlimited stability under load are therefore desired.

This object is achieved in that the base of the U-shaped recess has a curved portion in a direction perpendicular to the U-shaped cross-section. As a consequence, round rods which are bent corresponding to the form correction can be used in place of the plate members for the form correction proper, because even bent rods can be perfectly fastened within the anchoring members. Moreover, the stability under continuous load is considerably increased for straight rods, but in particular also for curved rods.

Further features and advantages of the invention will be evident from the description of embodiments with reference to the drawings.

In the drawings:

FIG. 1 shows a side view of a first embodiment of the anchoring member;

FIG. 2 is a front view of the apparatus shown in FIG. 1;

FIG. 3 shows a section along line III—III in FIG. 1;

FIG. 4 shows a section along line IV—IV in FIG. 2;

FIG. 5 is a side view of a second embodiment;

FIG. 6 shows a section along the plane of symmetry of a modified embodiment in exploded representation;

Figure 7:
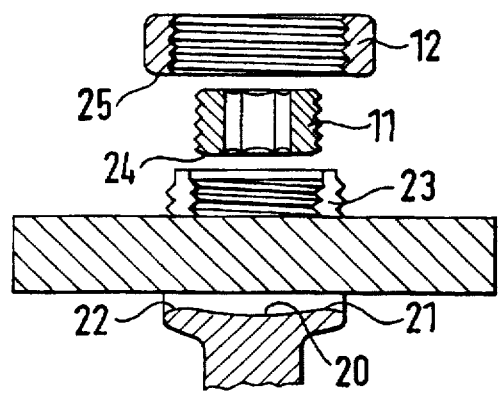
Figure 8:
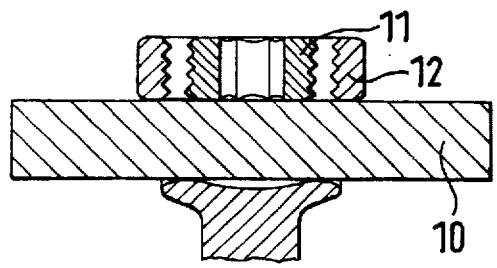
Figure 9:
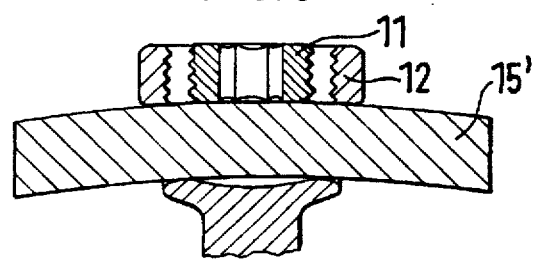

FIG. 8 corresponds to FIG. 7 with mounted straight rod;

FIG. 9 shows the same embodiment with a convexly curved rod; and

Figure 10:
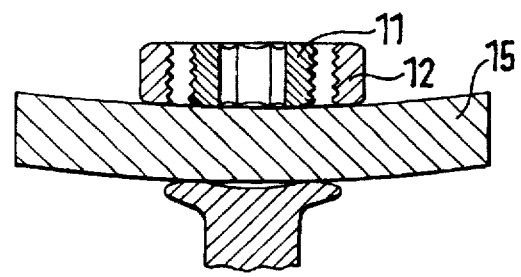

FIG. 10 shows the same embodiment with a concavely curved rod.

The anchoring member shown in FIG. 1 comprises a screw 1 to be introduced into a spinal column and having a threaded shaft 2 and a head 3. The head 3 comprises a U-shaped recess 4 which is symmetric with respect to the central axis of the threaded shaft 2 and which has a base 5 directed towards the threaded shaft 2. The lateral wall of the head defining the U-shaped recess 4 is formed by free legs 6, 7. As best shown in FIGS. 3, 4 and 5 a bore which is coaxial with the center axis of the threaded shaft 2 and has an internal thread 8 is provided in the interior of the channel. The head 3 itself is cylindrical and comprises an external thread 9 at the region of the free legs 6, 7, as best shown in FIG. 4.

In order to allow a rod to be anchored by means of this screw a fastening member 11 formed as a threaded bolt is provided. The fastening member 11 comprises an external thread cooperating with the internal thread 8 for screwing into the U-shaped recess 4. The fastening member has a slit or any other suitable recess for engagement of a screw driver formed at its face opposite to the base 5. Further, a surrounding member embracing both U-shaped legs 6, 7 at their outer side is formed as a spigot 12 having a thread which cooperates with the external thread 9. The sense of rotation of the internal thread 8 and of the associated fastening member 11 is opposite to that of the external thread 9 and of the spigot 12. As best shown in FIG. 3 the base 5 of the U-shaped recess has a radius which is larger than the radius of the rod 10 to be received therein by such a slight amount only that the rod may easily be inserted into the U-shaped recess and removed therefrom, resp. Both the internal thread 8 and the external thread 9 extend as far downwards, i.e. in direction of the basis 5, that the projection onto the axis of symmetry is spaced from the base 5 by a distance which is smaller than the diameter of the rod 10 to be received.

In the embodiment shown in FIG. 5 the head is connected to a shaft formed as a hook 16 rather than to a threaded shaft. This shaft as well serves for connection to a member of the spinal column wherein the hook is introduced into the arch of a vertebra.

In the embodiment shown in FIG. 6 the base of the U-shaped recess comprises a countersunk hole 17 coaxial with the center axis of the internal thread 8. The two rims 18, 19 of the base are cambered sloping outwardly towards the shaft. Hence, when receiving a curved rod a larger support area is formed on the base of the U-shaped recess 4 rather than a punctual support only. The camber towards the shaft serves to the purpose of ensuring a better form fit with a rod curved towards the shaft.

In FIGS. 7 to 10 the head of a further embodiment is shown in connection with a rod to be connected thereto. The shaft connected to the head may be formed as a threaded shaft 2 or as a hook 16.

As shown in the figures the base of the respective U-shaped recess is curved. The curvature comprises an inner concave portion 20 and symmetrically thereto with respect to the center axis of the screw two upwardly projecting cambered regions 21, 22. The distance of the respective topmost portion of the bead-shaped projections 21 and 22 from the center axis of the screw is substantially equal to the distance of the center 23 between the radius of the internal thread 8 and the radius of the external thread 9 from the center axis of the screw.

As best shown in FIGS. 1, 3 and 5 the head 3 comprises two recesses 13, 14 which are offset with respect to each other by 180° and by substantially 90° with respect to the U-shaped recess and serve for engagement of a tool such as gripping pliers.

In operation the screw 1 is first screwed into the spinal column. Thereupon the rod 10 or 15, 15' is placed into the U-shaped recess 4 and fastened by screwing the fastening member 11 into the thread 8. Thereafter the spigot 12 is screwed on. Now the fastening member and the spigot 12 are separately rotated towards the base 5 to such an extent that each one of the two parts exerts a desired retaining force onto the rod 10, 15, 15'. Thereby the advantage is achieved that the fixation by a fastening member 11 and the fixation by spigot 12 with respect to the rod are both separately adjustable. Moreover a final fixation and locking of the screw by clamping is obtained as the tightening of the fastening member and the spigot fixes the rod in place and the exertion of a force by the fastening member on the rod causes a force of the legs against the spigot to fix the three elements together.

Owing to the curved shape of the base of the U-shaped recess and in particular to the shape shown in the FIGS. 7 to 10 having the spaced projecting cambered support regions and their above-described position it is achieved that each rod to be fastened, whether it is formed as a straight rod 10 or as a convexly or concavely curved rod 15, 15', rests upon two planar regions 21, 22. As best shown in FIG. 7 the lower edges 24, 25 of the fastening member 11 and of the spigot 12 facing the rod are additionally rounded or convexly curved. As a result all points of engagement contacting the rod to be fastened act upon the rod without using sharp edges. Moreover, the described position results in a positioning of the engagement region of both projecting regions 21, 22 of the base exactly between the points of engagement of the fastening member 11 and of the spigot 12. In this manner a particularly good fixation and a particularly low strain is achieved. As best shown in FIGS. 8 to 10 the good fixation is achieved for any kind of curvature of the rods 10, 15, 15'. In the aforementioned embodiments the head 3 is rigidly connected with the threaded shaft or the hook-shaped shaft, resp. According to a modified embodiment the respective shaft and the head are connected through a hinge.

We claim:

1. An anchoring member for attachment to a vertebra, the anchoring member comprising:

a head having a U-shaped channel with two legs and an open end, said legs having an internal thread and an external thread, a fastening member having an external thread engaging the internal thread of said legs, a spigot open at the top and bottom and having an internal thread engaging the external thread of the legs, the fastening member and the spigot being structured and arranged to engage the surface of a rod, the internal and external threads of the head having a length to permit the fastening member and spigot to engage the rod whereby the tightening of the fastening member and the spigot fixes the rod in place and the exertion of an expanding force by the fastening member on the rod causes a force on the legs against the spigot to fix together the head, the fastening member and the spigot.

2. The anchoring member of claim 1, wherein the spigot has a top and bottom with smooth surfaces.

3. The anchoring member of claim 1, wherein the fastening member has a top and bottom with smooth surfaces.

4. The anchoring member of claim 1, wherein the U-shaped channel has a bottom which has a beveled shape.

5. The anchoring member of claim 1, wherein the U-shaped channel has a bottom which comprises a depressed portion and an outwardly projecting curved portion positioned on each side of said depressed portion.

6. The anchoring member of claim 1, wherein the anchoring member further comprises a threaded shaft.

7. The anchoring member of claim 1, wherein the anchoring member further comprises a hook portion.

* * * * *

UNITED STATES PATENT AND TRADEMARK OFFICE
CERTIFICATE OF CORRECTION

PATENT NO.: 5,725,527

DATED: March 10, 1998

INVENTOR(S): Biedermann et al.

It is certified that error appears in the above-identified patent and that said Letters Patent is hereby corrected as shown below:

On the cover page, first column, after "[30] Foreign Application Priority Data, please change "Sep. 10, 1992" to --Oct. 9, 1992--.

On the cover page, second column, please delete the third line, which reads: "0441791A1   2/1991   European Pat. Off."

Signed and Sealed this

Ninth Day of June, 1998

Attest:

BRUCE LEHMAN

Attesting Officer

Commissioner of Patents and Trademarks